United States Patent

Meng et al.

Patent Number: 5,856,510
Date of Patent: Jan. 5, 1999

[54] 5-ALKENYL AND 5-ALKYNYL INDOLE COMPOUNDS

[75] Inventors: Oingchang Meng, Georgetown; Abdelmalik Slassi, Mississauga; Louise Edwards, Mississauga; Sumanas Rakhit, Misssissauga, all of Canada

[73] Assignee: Allelix Biopharmaceuticals Inc., Mississauga, Canada

[21] Appl. No.: 767,322

[22] Filed: Dec. 16, 1996

[51] Int. Cl.[6] ........................ C07D 403/02; C07D 209/02; C07D 209/04; C07D 209/16; A61K 31/415; A61K 31/405

[52] U.S. Cl. ...................... 548/312.1; 514/397; 514/415; 548/468; 548/469; 548/491; 548/504

[58] Field of Search ........................ 548/491, 504, 548/312.1, 468, 469; 514/397, 415

[56] References Cited

U.S. PATENT DOCUMENTS

| | | | |
|---|---|---|---|
| 4,870,085 | 9/1989 | Glaser et al. | 514/323 |
| 5,348,968 | 9/1994 | Lavielle et al. | 514/360 |
| 5,496,957 | 3/1996 | Glennon | 548/491 |
| 5,504,101 | 4/1996 | Glennon | 514/415 |

FOREIGN PATENT DOCUMENTS

| | | |
|---|---|---|
| 02037351B | 8/1990 | Japan. |
| WO 9402477 | 2/1994 | WIPO. |
| WO 9424127 | 10/1994 | WIPO. |
| WO 9617842 | 6/1996 | WIPO. |

OTHER PUBLICATIONS

Glen, et al. Journal of Medicinal Chemistry, 1995, 38:3566–3580.

"Computer–Aided Design and Synthesis of 5–Substituted Tryptamines and Their Pharmacology at the 5–HT1D Receptor: Discovery of Compounds with Potential Anti–Migraine Properties".

*Primary Examiner*—Floyd D. Higel
*Attorney, Agent, or Firm*—Nikaido, Marmelstein, Murray & Oram LLP

[57] ABSTRACT

Described herein are compounds selective for $5\text{-}HT_{1D}$-like receptors, which have the general formula:

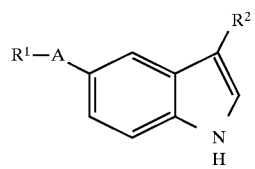

I wherein:

$R^1$ is selected from H, aryl and aryl substituted with 1, 2 or 3 substituents independently selected from loweralkyl, loweralkoxy, loweralkylcarbonyl, loweralkyl-S—, loweralkyl-S(O)—, loweralkyl-$SO_2$-, S=C=N—, O=C=N—, halo, loweralkoxycarbonyl, nitro, amino, loweralkyl-NH—, (loweralkyl)$_2$—N—, loweralkyl-$SO_2$-loweralkyl-;

A is a double or triple bond;

$R^2$ is selected from a group of Formula II, III, IV and V:

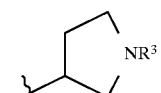

II

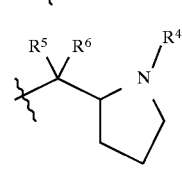

III

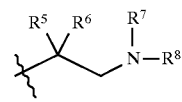

IV

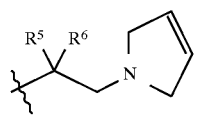

V $R^3$ is selected from H and loweralkyl;

$R^4$ is selected from H and loweralkyl;

One of $R^5$ and $R^6$ is H and the other is independently selected from H, loweralkoxy, loweralkyl and hydroxy; and $R^7$ and $R^8$ are independently selected from H and loweralkyl or $R^7$ and $R^8$, together with the nitrogen atom to which they are attached, form an optionally substituted 3- to 6-membered ring;

or a salt, solvate or hydrate thereof.

Also described is the use of these compounds as pharmaceuticals to treat indications where stimulation of the $5\text{-}HT_{1D}$-like receptor is implicated, such as migraine.

30 Claims, No Drawings

5-ALKENYL AND 5-ALKYNYL INDOLE COMPOUNDS

This invention relates to 5-alkenyl- and 5-alkynyl-substituted indole compounds, to pharmaceutical compositions containing them and to their medical use, particularly in the treatment of CNS conditions.

According to one aspect of the invention, there are provided compounds of Formula I and salts, solvates or hydrates thereof:

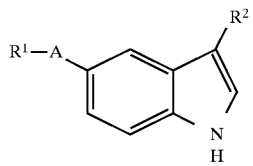

wherein:
$R^1$ is selected from H, aryl and aryl substituted with 1, 2 or 3 substituents independently selected from loweralkyl, loweralkoxy, loweralkylcarbonyl, loweralkyl-S—, loweralkyl-S(O)—, loweralkyl-SO$_2$-, S=C=N—, O=C=N—, halo, loweralkoxycarbonyl, nitro, amino, loweralkyl-NH—, (loweralkyl)$_2$-N—, loweralkyl-SO$_2$-loweralkyl- and pyrrolo;
A is a double or triple bond;
$R^2$ is selected from a group of Formula II, III, IV and V:

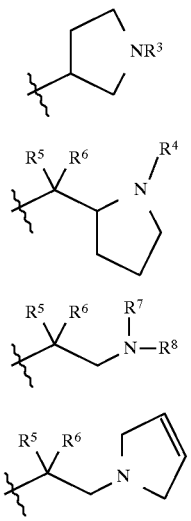

$R^3$ is selected from H and loweralkyl;
$R^4$ is selected from H and loweralkyl;
One of $R^5$ and $R^6$ is H and the other is independently selected from H, loweralkoxy, loweralkyl and hydroxy; and $R^7$ and $R^8$ are independently selected from H and loweralkyl or $R^7$ and $R^8$, together with the nitrogen atom to which they are attached, form an optionally substituted 3- to 6-membered ring.

According to another aspect of the invention, there is provided a pharmaceutical composition comprising a compound of Formula I in an amount effective to stimulate 5-HT$_{1D}$-like receptors, and a pharmaceutically acceptable carrier.

In another aspect of the present invention there are provided compositions containing the present compounds in amounts for pharmaceutical use to treat CNS conditions where a 5-HT$_{1D}$-like ligand is indicated. These and other aspects of the present invention are described in greater detail hereinbelow.

DETAILED DESCRIPTION AND PREFERRED EMBODIMENTS

The term "loweralkyl" as used herein means straight and branched chain alkyl radicals containing from one to six carbon atoms and includes methyl, ethyl, propyl, isopropyl, tert-butyl and the like.

The term "loweralkoxy" as used herein means straight and branched chain alkoxy radicals containing from one to four carbon atoms and includes methoxy, ethoxy, tert-butoxy and the like.

The term "aryl" as used herein means a 5 or 6 membered aromatic ring or heteroaromatic ring containing 1, 2 or 3 heteroatoms independently selected from O, N and S, and includes phenyl, pyridyl, thienyl, furanyl, pyrrolo, imidazolo and the like.

The term "vinyl" as used herein means a double bond. The term "alkynyl" as used herein means a triple bond.

Compounds of Formula I include those in which, $R^1$ is selected from H, aryl and aryl substituted with 1, 2 or 3 substituents independently selected from loweralkyl, loweralkoxy, loweralkylcarbonyl, loweralkyl-S—, loweralkyl-S(O)—, loweralkyl-SO$_2$-, S=C=N—, O=C=N—, halo, loweralkoxycarbonyl, nitro, amino, loweralkyl-NH—, (loweralkyl)$_2$-N—, loweralkyl-SO$_2$-loweralkyl- and pyrrolo. In preferred embodiments, $R^1$ is selected from H and phenyl, thienyl, imidazolo all optionally substituted with 1, 2 or 3 substituents independently selected from loweralkyl, loweralkoxy, loweralkylcarbonyl, loweralkyl-S—, loweralkyl-SO$_2$-, S=C=N—, halo, loweralkoxycarbonyl, nitro, loweralkyl-SO$_2$-loweralkyl- and pyrrolo. In more preferred embodiments, $R^1$ is selected from H, thienyl, 4-(isothiocyanato)phenyl, 4-(pyrrol-1-yl) phenyl, 4-methylphenyl, 4-(isopropylsulfonyl)-2-(methylcarboxylate)-thienyl, 1-[2-(ethylsulfonyl)ethyl]-2-methyl-4-nitroimidazol-5-yl, 2-(methylthio)phenyl, acetophenonyl and 5-chloro-2-methoxyphenyl. In the most preferred embodiment $R^1$ is H.

In another embodiment of the invention, $R^2$ is selected from a group of Formula II, III, IV and V:

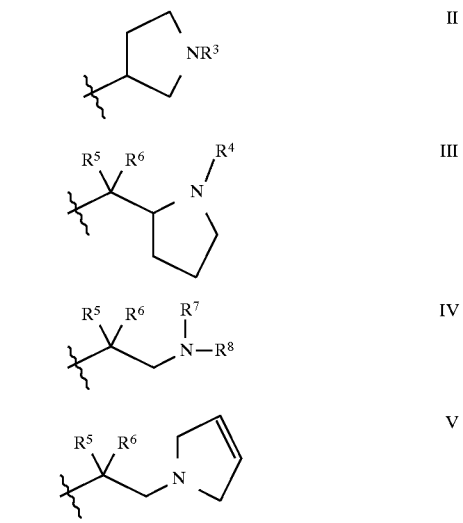

In preferred embodiments, $R^2$ is selected from a group of Formula IV and V. In a more preferred embodiment, $R^2$ is a group of Formula IV.

When $R^2$ is a group of Formula II, $R^3$ is selected from H and loweralkyl. Preferably $R^2$ is loweralkyl, specifically, methyl. When $R^2$ is a group of Formula III, $R^4$ is selected from H and loweralkyl. In preferred embodiments, $R^4$ is loweralkyl, specifically, methyl. When $R^2$ is a group of Formula IV, one of $R^5$ and $R^6$ is H and the other is independently selected from H, loweralkoxy. loweralkyl and hydroxy and $R^7$ and $R^8$, together with the nitrogen atom to which they are attached, form a 3- to 6-membered, desirably saturated, ring optionally substituted with one or two groups selected from loweralkyl, hydroxy and loweralkoxy. In preferred embodiments, when $R^2$ is a group of Formula IV, $R^5$, $R^6$, $R^7$ and $R^8$ are selected to provide

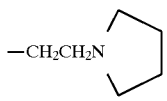

or $CH_2CH_2NMe_2$. When $R^2$ is a group of Formula V, one of $R^5$ and $R^6$ is H and the other is independently selected from H, loweralkoxy and hydroxy; preferably $R^5$ and $R^6$ are both H.

In specific embodiments of the invention, the compounds of Formula I include:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole;
3-(N-Methylpyrrolidin-3-yl)-5-vinyl-1H-indole;
5-Ethynyl-3-(2-pyrrolidinylethyl)-1H-indole;
3-(2-N,N-Dimethylaminoethyl)-5-[2-(thien-2-yl)ethynyl]-1H-indole;
5-{2-[4-(isothiocyanato)phenyl]ethynyl}-3-(2-pyrrolidinylethyl)-1H-indole;
3-(2-Pyrrolidinylethyl)-5-{2-[4-(pyrrol-1-yl)phenyl]ethynyl}-1H-indole;
5-[2-(4-Methylphenyl)ethynyl]-3-(2-pyrrolidinylethyl)-1H-indole;
5-{2-[4-(isopropylsulfonyl)-2-(methylcarboxylate)-thien-3-yl]ethynyl}-3-(2-pyrrolidinylethyl)-1H-indole;
5-{2-[1-(2-(Ethylsulfonyl)ethyl)-2-methyl-4-nitroimidazol-5-yl]ethynyl}-3-(2-pyrrolidinylethyl)-1H-indole;
5-{2-[2-(Methylthio)phenyl]ethynyl}-3-(2-pyrrolidinylethyl)-1H-indole;
5-[2-(Acetophenon-4-yl)ethynyl]-3-(2-pyrrolidinylethyl)-1H-indole;
3-(2-Pyrrolidinylethyl)-5-[2-(thien-2-yl)ethynyl]-1H-indole; and
5-[2-(5-Chloro-2-methoxyphenyl)ethynyl]-3-(2-pyrrolidinylethyl)-1H-indole.

In preferred embodiments of the invention, the compounds of Formula I include:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole;
3-(N-Methylpyrrolidin-3-yl)-5-vinyl-1H-indole;
5-Ethynyl-3-(2-pyrrolidinylethyl)-1H-indole;
5-{2-[4-(isothiocyanato)phenyl]ethynyl}-3-(2-pyrrolidinylethyl)-1H-indole;
3-(2-Pyrrolidinylethyl)-5-{2-[4-(pyrrol-1-yl)phenyl]ethynyl}-1H-indole;
5-{2-[1-(2-(Ethylsulfonyl)ethyl)-2-methyl-4-nitroimidazol-5-yl]ethynyl}-3-(2-pyrrolidinylethyl)-1H-indole; and
5-[2-(5-Chloro-2-methoxyphenyl)ethynyl]-3-(2-pyrrolidinylethyl)-1H-indole.

In the most preferred embodiments of the invention, the compounds of Formula I include:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole; and
5-Ethynyl-3-(2-pyrrolidinylethyl)-1H-indole.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Some of the compounds of the present invention have chiral centres, e.g. those in which one of $R^5$ and $R^6$ is hydroxy or loweralkoxy and those in which $R^2$ is a group of Formula II or III. Also, it will be appreciated that when A is a double bond, the stereochemistry about this double bond may be cis or trans. The invention extends to cover all structural and optical isomers of the various compounds, as well as stereochemical and racemic mixtures thereof.

The compounds of the present invention can be prepared by processes analogous to those established in the art. Therefore, in general, compounds of Formula I can be prepared by first coupling either an indole of Formula B, wherein X is a suitable leaving group such as halo or triflate (preferably bromo) and $R^9$ is group of Formula VI, VII, VII or IX, or an indole of Formula C, wherein X is as described above, $R^2$ is as defined for Formula I and PG is a suitable protecting group (preferably p-toluenesulfonate), with a vinyl or alkynyl metal reagent of Formula D, wherein M is an optionally substituted metal substituent and $R^{10}$ is either $R^1$ or a suitable protecting group such as trialkylsilyl (preferably triethylsilyl). This coupling reaction can be conducted under standard palladium catalyzed-cross coupling conditions to provide intermediates E and F respectively, as shown in Scheme 1. Examples of M groups are described in Synthesis, 1991, pages 413–432 and in references cited therein, and include $(alkyl)_3Sn$—, (alkyl)$_2B$—, $(HO)_2B$—, $(alkoxy)_2B$—, Li—, Cu—, chlorozinc-, haloMg- and the like. The most preferred M groups are $(alkyl)_3Sn$ and Cu—. The reaction takes place in an inert solvent, usually in the presence of base, a suitable catalyst and, optionally, lithium chloride. The choice of catalyst varies to some extent with the choice of group M and the structure of the substituted indole reagent. Suitable catalysts are palladium (II) and palladium (0) species such as palladium (II) acetate, palladium (II) chloride, bis(triphenylphosphine)palladium (II) chloride and tetrakis(triphenylphosphine)palladium (0). The preferred catalysts are bis(triphenylphosphine)palladium (II) chloride and tetrakis(triphenylphosphine)palladium (0). Suitable bases include tertiary amines, sodium bicarbonate and sodium carbonate, with triethylamine being preferred. Suitable inert solvents include N,N-dimethylformamide, toluene, acetonitrile and 1,2-dimethoxyethane, with N,N-dimethylformamide and toluene being preferred. The reaction can take place at a temperature of from 50°–120° C., preferably at from 90°–110° C.

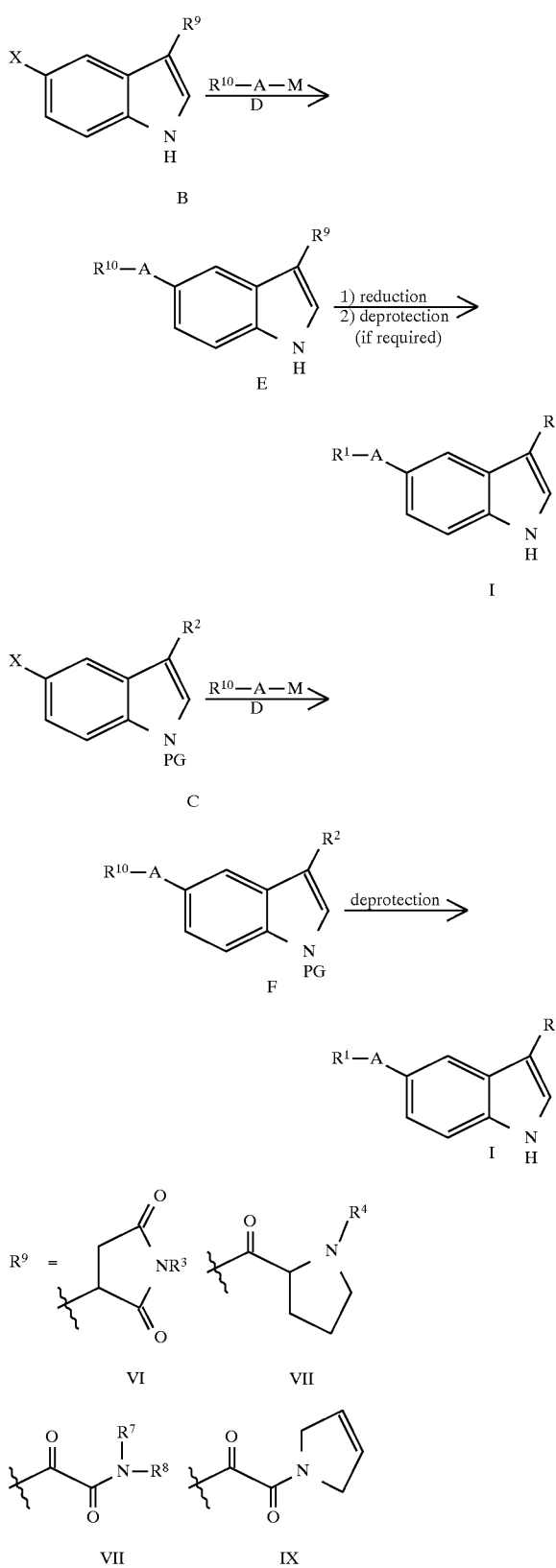

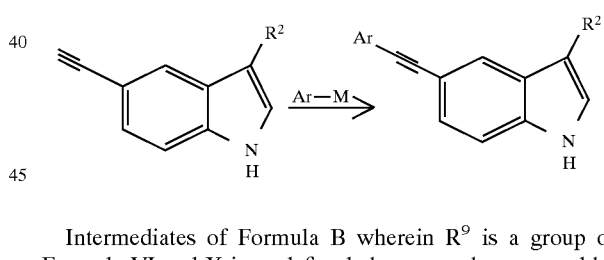

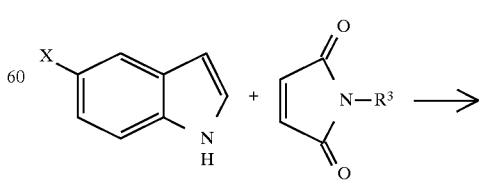

Intermediate E can be reduced and, if $R^{10}$ is a protecting group, deprotected to provide compounds of Formula I. The reduction can be performed using lithium aluminum hydride, lithium borohydride or diborane as reducing agent, in an inert solvent such as tetrahydrofuran, dioxane or diethyl ether at temperatures of from about 25°–100° C. Preferred is the reduction with lithium aluminum hydride in tetrahydrofuran at a temperature of about 65° C. If this reduction is carried out with a smaller amount of reducing agent, compounds of Formula I, wherein one of $R^5$ and $R^6$ is independently hydroxyl, can be isolated. This hydroxy group can then be alkylated using standard conditions (for example alkyl halide and potassium carbonate in acetonitrile) or displaced with, for example, loweralkyl lithium reagents, to provide compounds of Formula I wherein one of $R^5$ and $R^6$ is loweralkoxy or loweralkyl respectively. Deprotection can be conducted using standard procedures, for example, when the protecting group is trialkylsilyl, by treatment with fluoride ion in an inert solvent or strong base. Preferred is deprotection using potassium hydroxide in methanol at refluxing temperatures. When the protecting group on the indole nitrogen of intermediates F is, for example p-toluenesulfonate, it may be removed using strong base, for example potassium hydroxide in methanol at refluxing temperatures, to provide compounds of Formula I.

An alternative route to compounds of Formula I, wherein $R^1$ is substituted or unsubstituted aryl and A is a triple bond, involves coupling a compound of Formula I wherein $R^1$ is H and A is a triple bond, with an aryl-M reagent, wherein M is as defined above, under standard palladium cross-coupling conditions as shown in Scheme 2. These conditions are described above and preferably involve reacting the indole and metal reagent in the presence of triethylamine and bis(triphenylphosphine) palladium (II) chloride in toluene at refluxing temperatures.

Intermediates of Formula B wherein $R^9$ is a group of Formula VI and X is as defined above, can be prepared by condensing 5-substituted indole G, wherein X is as defined above, with maleimide H, wherein $R^3$ is as defined for Formula I, under acidic conditions at temperatures ranging from about 65°–155° C., as shown in Scheme 3. Preferred conditions are acetic acid at temperatures of about 100°–110° C.

-continued

Scheme 3

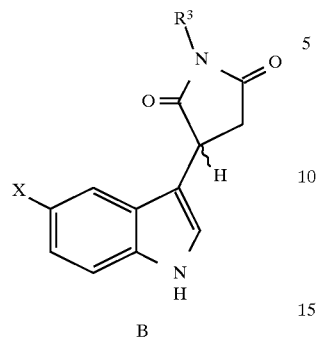

B (which is preferred). The reaction can be conducted at temperatures ranging from −30° to 65° C., suitably at room temperature. Intermediate K can be deprotected under standard conditions, for example sodium hydroxide in methanol, to provide intermediates L (compounds of Formula I where $R^4$ is hydrogen). Intermediate L can then be alkylated on the pyrrolidine nitrogen by treatment with $R^4$—X, wherein $R^4$ is loweralkyl and X is a suitable leaving group such as halogen, in the presence of a base in an inert solvent to provide intermediates B. Suitable alkylation conditions include potassium carbonate in acetonitrile or triethylamine in dichloromethane. Temperatures can be in the range of 25° to 85° C., preferably at room temperature.

Intermediates of Formula B, wherein $R^9$ is a group of Formula VII, can be prepared as shown in Scheme 4.

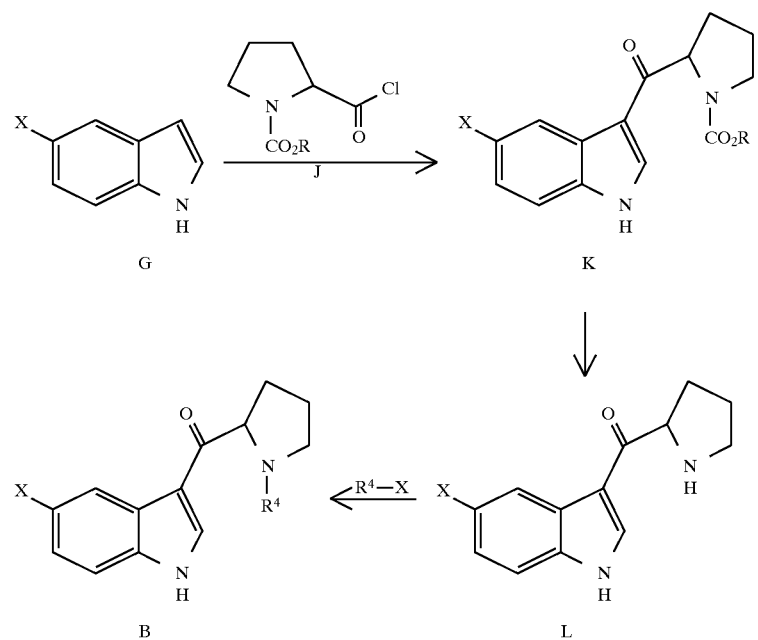

Scheme 4

Reagent J, in which R is, for example, benzyl or t-butyl, can be condensed with 5-substituted indole G, typically by first converting the indole to a magnesium derivative by reaction with a suitable Grignard reagent, such as t-butyl- or ethyl-magnesium bromide, in an inert solvent. Then the magnesium derivative so formed can be reacted in situ with a reagent of Formula J to provide intermediates of Formula K. Suitable solvents include tetrahydrofuran and diethylether To provide intermediates of Formula B wherein $R^9$ is a group of Formula VII or IX, indole G can be treated with oxalyl chloride and then the appropriate amine to provide compounds of formula B, wherein $R^7$ and $R^8$ are as defined for Formula I, as shown in Scheme 5. This reaction can be conducted in an inert solvent such as diethyl ether (preferred) or dichloromethane, and at temperatures in the range of 0°–65° C., preferably 25°–65° C.

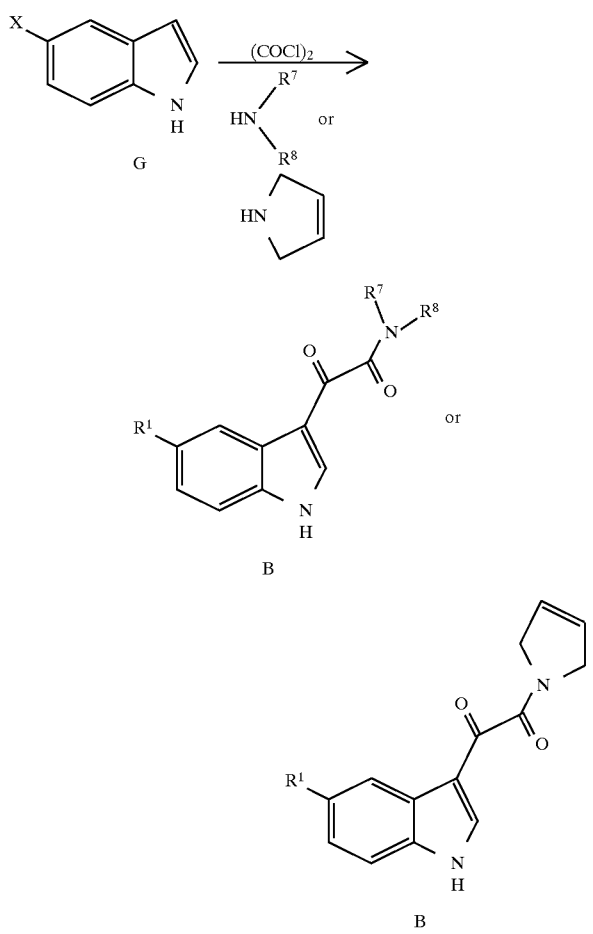

In an embodiment of the invention, the compound is provided in labeled form, such as radiolabeled form, e. g. labeled by incorporation within its structure $^3$H or $^{14}$C or by conjugation to $^{125}$I. In another aspect of the invention, the compounds in labeled form can be used to identify 5-HT$_{1D}$-like receptor ligands by techniques common in the art. This can be achieved by incubating the receptor or tissue in the presence of a ligand candidate and then incubating the resulting preparation with an equimolar amount of radiolabeled compound of the invention such as [$^3$H]-(R)-3-[(N-methylpyrrolidin-2-yl)methyl]-5-vinyl-1H-indole. 5-HT$_{1D}$-like receptor ligands are thus revealed as those that are not significantly displaced by the radiolabeled compound of the present invention. Alternatively, 5-HT$_{1D}$-like receptor ligand candidates may be identified by first incubating a radiolabeled form of a compound of the invention then incubating the resulting preparation in the presence of the candidate ligand. A more potent 5-HT$_{1D}$-like receptor ligand will, at equimolar concentration, displace the radiolabeled compound of the invention.

The present compounds are useful as pharmaceuticals for the treatment of various conditions in which the use of a 5-HT$_{1D}$-like ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 1 to 25 mg) of a compound of Formula I or IV or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous or intramuscular dose of between 0.1 mg and 100 mg, preferably between 0.1 mg and 50 mg, e.g., between 1 mg and 25 mg, of a compound of Formula I or IV or a pharmaceutically acceptable salt, solvate or hydrate thereof calculated as the free base, the compound being administered 1 to 4 times per day. Suitably, the compounds will be administered for a period of continuous therapy, for example for a week or more.

EXAMPLE 1(a)

5-Bromo-3-[(N-pyrrolidinyl)glyoxyl]-1H-indole

To a solution of 5-bromoindole (3.92 g, 20 mmol) in ether (50 mL), cooled to 0° C., was added a solution of oxalyl chloride in dichloromethane (2M, 10 mL) dropwise. The resulting mixture was stirred at room temperature overnight and then cooled to 0° C. and pyrrolidine (6.7 mL, 80 mmol) was added dropwise. After stirring for 2 hours at room temperature, the mixture was poured into water (50 mL) and extracted with dichloromethane (3×100 mL). The combined organic phases were dried over sodium sulfate and evaporated to a white amorphous solid which was washed with ethyl acetate (50 mL) to give 5-bromo-3-[(N-pyrrolidinyl)glyoxyl]-1H-indole (2.87 g, 45%). mp 212°–213° C.; $^1$H NMR (CDCl$_3$, 300 MHz) d: 10.69 (s, 1H), 8.49 (d, J=1.5 Hz, 1H), 7.87 (d, J=3.0 Hz, 1H), 7.31 (dd, J=8.6, 1.5 Hz, 1H), 7.17 (d, J=8.6 Hz, 1H), 3.59 (m, 4H), 1.94 (m, 4H).

In a like manner, the following additional compound was prepared: (b) 5-Bromo-3-[(N,N-dimethylamino)glyoxyl]-1H-indole: from N,N-dimethylamine $^1$H NMR (CDCl$_3$, 300 MHz) δ: 10.05 (s, 1H), 8.48 (d, J=1.5 Hz, 1H), 7.71 (d, J=2.4 Hz, 1H), 7.35 (dd, J=1.5, 8.5 Hz, 1H), 7.19 (d, J=8.5 Hz, 1H), 3.10 (s, 3H), 3.06 (s, 3H).

EXAMPLE 2

5-Bromo-3-(2-pyrrolidinylethyl)-1H-indole

A solution of LAH (36 mL, 1M in THF, 36 mmol) was added slowly to a cooled (0° C.) solution of 5-bromo-3-[(N-pyrrolidinyl)glyoxyl]-1H-indole (Example 1a, 2.87 g, 8.9 mmol) in THF (100 mL). Once the addition was completed, the reaction mixture was stirred at reflux overnight prior to quenching with sodium sulfate decahydrate. The product was taken into ethyl acetate, filtered to remove the solid residue, and the solvent was removed in vacuo to yield the title compound (2.08 g, 72%).

EXAMPLE 3

(R)-3-(N-Benzyloxycarbonylpyrrolidin-2-ylcarbonyl)-5-bromo-1H-indole

To a stirred solution of N-benzyloxycarbonyl-R-proline (2.5 g, 10.0 mmol) in anhydrous methylene chloride was added a solution of oxalyl chloride (2M solution in methylene chloride, 7 mL, 15.0 mmol). The resulting mixture was stirred at room temperature under argon for 2 hours. The solvent and excess oxalyl chloride were evaporated under reduced pressure and the crude product washed with hexane (3×10 mL) and evaporated to dryness to provide N-benzyloxycarbonyl-R-proline acid chloride which was used directly for the next reaction.

N-Benzyloxycarbonyl-R-proline acid chloride from the above reaction was dissolved in anhydrous diethyl ether (30 mL) and added at 0° C. to a solution of 5-bromoindole (2.9 g, 15.0 mmol) and t-butylmagnesium chloride (2M solution in diethyl ether, 8.3 mL, 16.5 mmol) in anhydrous diethyl ether (30 mL). The resulting mixture was stirred at room temperature under argon for 45 minutes and then ethyl acetate (150 mL) and saturated sodium bicarbonate (30 mL) were added. The organic layer was dried and evaporated under reduced pressure to provide a yellow oil. The title compound was crystallized using hexane/ethyl acetate (9:1) to provide a white solid (3.07 g, 72%). mp 95°–96° C.

EXAMPLE 4

3-(5-Bromo-1H-indol-3-yl)-N-methylsuccinimide

To a solution of 5-bromoindole (5 g, 25.5 mmol) in glacial acetic acid (60 mL) was added N-methylmaleimide (6.1 g, 56.11 mmol) and the resulting mixture was heated to reflux for 4 days. The acetic acid was removed by distillation and the crude product was dissolved in diethyl ether (500 mL) and washed with saturated sodium bicarbonate (2×100 mL) and brine (3×100 mL). The solvent was evaporated and the residue chromatographed on silica gel using hexane/ethyl acetate (1:1) as the eluent to provide 3-(5-bromo-1H-indol-3-yl)-N-methylsuccinimide (5.85 g, 75%). Yellow solid, mp 194°–195° C.

EXAMPLE 5

5-Bromo-3-(2-pyrrolidinylethyl)-1-(p-toluenesulfonyl)-indole

To a solution of 5-bromo-3-(2-pyrrolidinylethyl)-1H-indole (Example 2, 9.10 g, 31 mmol) in tetrahydrofuran (100 mL) cooled to 0° C., were added sodium hydride (12.4 g, 310 mmol) and p-toluenesulfonyl chloride (6.10 g, 32 mmol). The resulting mixture was stirred at room temperature for 3 h, poured into water (200 mL) and extracted into ethyl acetate (200 mL). The organic phase was washed with water (200 mL) and then poured onto a silica gel column which was eluted with ethyl acetate followed by methanol. The title compound was obtained as a yellow syrup (11.7 g, 90%).

EXAMPLE 6(a)

3-(2-Pyrrolidinylethyl)-1-(p-toluenesulfonyl)-5-(triethylsilylethynyl)-indole

To a solution of 5-bromo-3-(2-pyrrolidinylethyl)-1-(p-toluenesulfonyl)-indole (Example 5, 415 mg, 1 mmol) in toluene (20 mL), were added triethylsilylacetylene (0.72 mL, 4 mmol, dichlorbis(triphenylphosphine) palladium (II) (210 mg, 0.3 mmol), copper (I) iodide (57 mg, 0.3 mmol) and triethylamine (1 mL). The resulting mixture was stirred under argon at reflux overnight and then evaporated to dryness. Chromatography on silica gel (ethyl acetate followed by methanol) gave the title compound as a yellow oil (197 mg, 39%).

In a like manner, the following additional compounds were prepared:
(b) 5-{2-[4-(isothiocyanato)phenyl]ethynyl}-3-(2-pyrrolidinylethyl)-1H-indole: from 5-ethynyl-3-(2-pyrrolidinylethyl)-1H-indole (Example 8) and 4-iodophenylisothiocyanate.
(c) 3-(2-Pyrrolidinylethyl)-5-{2-[4-(pyrrol-1-yl)phenyl]ethynyl}-1H-indole: from 5-ethynyl-3-(2- pyrrolidinylethyl)-1H-indole (Example 8) and 1-(4-iodophenyl)pyrrole.

(d) 5-[2-(4-Methylphenyl)ethynyl]-3-(2-pyrrolidinylethyl)-1H-indole: from 5-ethynyl-3-(2-pyrrolidinylethyl)-1H-indole (Example 8) and 4-iodotoluene.

(e) 5-{2-[4-(isopropylsulfonyl)ethynyl]-2-(methylcarboxylate)-thien-3-yl]-3-(2-pyrrolidinylethyl)-1H-indole: from 5-ethynyl-3-(2-pyrrolidinylethyl)-1H-indole (Example 8) and methyl 3-iodo-4-(isopropylsulfonyl)thiophene-2-carboxylate.

(f) 5-{2-[1-(2-(Ethylsulfonyl)ethyl)-2-methyl-4-nitroimidazol-5-yl]ethynyl}-3-(2-pyrrolidinylethyl)-1H-indole: from 5-ethynyl-3-(2-pyrrolidinylethyl)-1H-indole (Example 8) and 1-[2-(ethylsulfonyl)ethyl]-5-iodo-2-methyl-4-nitroimidazole.

(g) 5-{2-[2-(Methylthio)phenyl]ethynyl}-3-(2-pyrrolidinylethyl)-1H-indole: from 5-ethynyl-3-(2-pyrrolidinylethyl)-1H-indole (Example 8) and 2-(methylthio)iodobenzene.

(h) 5-[2-(Acetophenon-4-yl)ethynyl]-3-(2-pyrrolidinylethyl)-1H-indole: from 5-ethynyl-3-(2-pyrrolidinylethyl)-1H-indole (Example 8) and 4-iodoacetophenone.

(i) 5-[2-(5-Chloro-2-methoxyphenyl)ethynyl]-3-(2-pyrrolidinylethyl)-1H-indole: from 5-ethynyl-3-(2-pyrrolidinylethyl)-1H-indole (Example 8) and 5-chloro-2-methoxyiodobenzene.

(j) 3-(2-Pyrrolidinylethyl)-5-[2-(thien-2-yl)ethynyl]-1H-indole: from 5-ethynyl-3-(2-pyrrolidinylethyl)-1H-indole (Example 8) and 2-iodothiophene; HRMS-FAB$^+$ for $C_{18}H_{19}N_2S$: calculated MH$^+$: 295.12689; found MH$^+$: 295.12675.

EXAMPLE 7(a)

3-[2-(N,N-Dimethylamino)ethyl]-5-vinyl-1H-indole

A solution of 5-bromo-3-[(N,N-dimethylamino)glyoxyl]-1H-indole (Example 1b, 152 mg, 0.52 mmol), tributyl(vinyl)tin (0.18 mL, 0.62 mmol) and tetrakistriphenyphosphine palladium (0) (63 mg, 0.055 mmol) in anhydrous DMF (3 mL) was stirred at 100°–105° C. for 2 days. After cooling to room temperature, the product was taken into ethyl acetate, filtered through celite, washed with water (2×) and brine (1×), dried over sodium sulfate and the solvent was removed in vacuo. Flash chromatography on silica gel (75–100% ethyl acetate in hexanes) yielded 3-[(N,N-dimethylamino)glyoxyl]-5-vinyl-1H-indole (71 mg, 57%).

A solution of LAH (0.58 mL, 1M in THF, 0.58 mmol) was added slowly to a cooled (0° C.) solution of 3-[(N,N-dimethylamino)glyoxyl]-5-vinyl-1H-indole (70 mg, 0.29 mmol) in THF (5 mL). Once the addition was completed, the reaction mixture was stirred at reflux for 2 h prior to quenching with sodium sulfate decahydrate. The product was taken into ethyl acetate, filtered to remove the solid residue, and the solvent was removed in vacuo. Flash chromatography on silica gel (5% 2M methanolic ammonia in dichloromethane) yielded 3-[2-(N,N-dimethylamino)ethyl]-5-vinyl-1H-indole (38 mg, 61%). HRMS-FAB$^+$ for $C_{14}H_{18}N_2$: calculated MH$^+$: 215.15483; found MH$^+$: 215.15406.

In a like manner, the following additional compounds were prepared:

(b) 3-[2-(N-Pyrrolidinyl)ethyl]-5-vinyl-1H-indole: from 5-bromo-3-[(N-pyrrolidinyl)glyoxyl]-1H-indole (Example 1a) (7%, larger scale no purification of intermediate).

(c) (R)-3-[(N-Methylpyrrolidin-2-yl)methyl]-5-vinyl-1H-indole: from (R)-3-(N-Benzyloxycarbonylpyrrolidin-2-ylcarbonyl)-5-bromo-1H-indole (Example 3) (37% over 2 steps, HRMS-FAB$^+$ for $C_{16}H_{20}N_2$: calculated MH$^+$: 241.17047; found MH$^+$: 241.17036).

(d) 3-(N-Methylpyrrolidin-3-yl)-5-vinyl-1H-indole: from 3-(5-bromo-1H-indol-3-yl)-N-methylsuccinimide (Example 4) (27% over 2 steps, HRMS-FAB$^+$ for $C_{15}H_{18}N_2$: calculated MH$^+$: 227.15483; found MH$^+$: 227.15356).

EXAMPLE 8

5-Ethynyl-3-(2-pyrrolidinylethyl)-1H-indole 3-(2-Pyrrolidinylethyl)-1-(p-toluenesulfonyl)-5-(triethylsilylethynyl)-indole (Example 6a, 130 mg, 0.26 mmol) was mixed with 5% potassium hydroxide in methanol (20 mL) and stirred at reflux for up to 48 h. The solvent was evaporated to about 4 mL, poured into dichloromethane (40 mL), washed with brine (40 mL), dried over sodium sulfate and evaporated. Chromatography on silica gel (dichloromethane/methanol/ammonium hydroxide 50:7:1) gave the title compound as a yellow oil (41 mg, 66%). HRMS-FAB$^+$ for $C_{16}H_{19}N_2$: calculated MH$^+$: 239.15483, found MH$^+$: 239.15766.

SUMMARY OF EXEMPLIFIED COMPOUNDS OF FORMULA I

| Example # | R$^1$ | A | R$^2$ |
|---|---|---|---|
| 6b | SN=N=C— | alkynyl | pyrrolidinylethyl |
| 6c | pyrrol-1-yl-phenyl | alkynyl | pyrrolidinylethyl |
| 6d | CH$_3$-phenyl | alkynyl | pyrrolidinylethyl |

-continued

| Example # | R¹ | A | R² |
|---|---|---|---|
| 6e | isopropylsulfonyl-thiophene-methyl ester structure | alkynyl | propyl-pyrrolidine |
| 6f | O₂N-substituted imidazole with N-CH₃ and ethyl-SO₂-ethyl | alkynyl | propyl-pyrrolidine |
| 6g | 2-(SMe)phenyl | alkynyl | propyl-pyrrolidine |
| 6h | 4-acetylphenyl | alkynyl | propyl-pyrrolidine |
| 6i | 4-chloro-2-methoxyphenyl | alkynyl | propyl-pyrrolidine |
| 6j | 2-thienyl | alkynyl | propyl-pyrrolidine |
| 7a | H | vinyl | propyl-N(CH₃)₂ |
| 7b | H | vinyl | propyl-pyrrolidine |
| 7c | H | vinyl | (S)-2-(N-methylpyrrolidinyl)ethyl |
| 7d | H | vinyl | (N-methylpyrrolidin-3-yl)methyl |

| Example # | R¹ | A | R² |
|---|---|---|---|
| 8 | H | alkynyl | 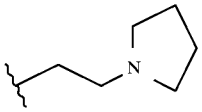 |

EXAMPLE 9

Agonist Assay

The in vitro evaluation of the 5-$HT_{1D}$-like receptor agonist activity of compounds of the invention was carried out by testing the extent to which they mimic sumatriptan, the marketed antimigraine drug, in contracting the rabbit saphenous vein (Perez, M. et al. J. Med. Chem. 1995, 38:3602–3607).

Tissues were obtained from male New Zealand White rabbits (~3–4 kg) which were sacrificed by an overdose of pentobarbital. The saphenous veins from both the left and right side were cleaned of fat and connective tissue and placed in Krebs solution (118 mM NaCl, 11 mM glucose, 25 mM $NaHCO_3$, 4.7 mM KCl, 2.5 mM $CaCl_2 2H_2O$, 1.2 mM $KH_2PO_4$, and 1.2 mM $MgSO_4 7H_2O$. Ring segments of the vein (4–5 mm in length) were cut and the endothelium gently removed. The segments were mounted in 10 mL baths containing Krebs buffer and were constantly aerated with 95% oxygen/5% carbon dioxide and maintained at 37° C. and pH 7.4 in order to record the isometric tension. A resting tension of 2.5 g was applied and the tissues allowed to equilibrate for 90 minutes, with washing every 15–20 minutes. After the equilibrium period, the rings were depolarized by the addition of two aliquots of KCl (80 mM final concentration) separated by a 20 minute washing period. The tissues were then exposed to prazosin, idazoxan and indomethacin (all 1 μM final concentration) for 30 minutes in order to exclude the actions of $\alpha_1$- and $\alpha_2$-adrenergic receptors and prostaglandin receptors respectively. Cumulative concentration-effect curves were then constructed for sumatriptan and the test compounds. Responses were calculated as a percentage of the maximal contraction evoked by 80 mM KCl. Only one compound was tested per preparation.

The following Table illustrates the in vitro activities for the compounds of the invention on the rabbit isolated saphenous vein. $EC_{50}$ represents the concentration of the compound which causes 50% of the maximum contraction effected by it.

| Compound/Example # | $EC_{50}$ (μM) |
|---|---|
| sumatriptan | 0.22 |
| 7c | 0.08 |
| 7d | 0.18 |
| 7b | 5.8 |
| 7a | 0.13 |

We claim:
1. A compound according to Formula I:

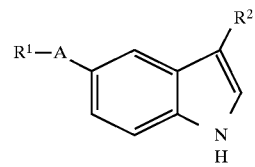

wherein:
R¹ is selected from the group consisting of H, aryl and aryl substituted with 1, 2 or 3 substituents independently selected from the group consisting of loweralkyl, loweralkoxy, loweralkylcarbonyl, loweralkyl-S—, loweralkyl-S(O)—, loweralkyl-$SO_2$-, S=C=N—, O=C=N—, halo, loweralkoxycarbonyl, nitro, amino, loweralkyl-NH—, (loweralkyl)$_2$-N—, and loweralkyl-$SO_2$-loweralkyl-;

A is —CH=CH— or —C≡C— (a vinyl or alkynyl group)

R² is selected from the group consisting of Formula II, III, IV and V:

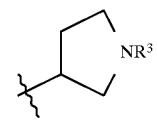

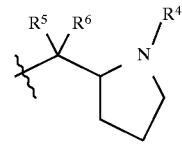

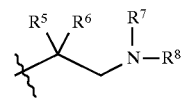

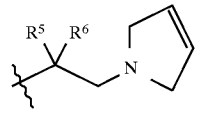

R³ is H or loweralkyl;
R⁴ is H or loweralkyl;
one of R⁵ and R⁶ is H and the other is independently selected from the group consisting of H, loweralkoxy, loweralkyl and hydroxy; and
R⁷ and R⁸ are independently selected from the group consisting of H and loweralkyl or R⁷ and R⁸, form an alkylene bridge which, together with the nitrogen atom to which they are attached, creates an unsubstituted or substituted 3- to 6-membered ring;
or a salt, solvate or hydrate thereof.

2. A compound according to claim 1, wherein R¹ is H.

3. A compound according to claim 1, wherein R¹ is selected from the group consisting of phenyl, thienyl, and imidazolo, wherein $R^1$ is either unsubstituted or substituted with 1, 2 or 3 substituents independently selected from the group consisting of loweralkyl, loweralkoxy, loweralkylcarbonyl, loweralkyl-S—, loweralkyl-$SO_2$, S=C=N—, halo, loweralkoxycarbonyl, nitro, loweralkyl-$SO_2$-loweralkyl- and pyrrolo.

4. A compound according to claim 3, wherein $R^1$ is selected from thienyl, 4-(isothiocyanato)phenyl, 4-(pyrrol-1-yl)phenyl, 4-methylphenyl, 4-(isopropylsulfonyl)-2-(methylcarboxylate)-thienyl, 1-[2-(ethylsulfonyl)ethyl]-2-methyl-4-nitroimidazol-5-yl, 2-(methylthio)phenyl, acetophenonyl and 5-chloro-2-methoxyphenyl.

5. A compound according to claim 2, wherein A is vinyl.

6. A compound according to claim 1, wherein $R^2$ is a group of Formula II.

7. A compound according to claim 6, wherein $R^3$ is methyl.

8. A compound according to claim 1, wherein $R^2$ is a group of Formula III.

9. A compound according to claim 8, wherein $R^4$ is methyl.

10. A compound according to claim 1, wherein $R^2$ is a group of Formula IV.

11. A compound according to claim 10, wherein $R^5$ and $R^6$ are both H.

12. A compound according to claim 11, wherein $R^7$ and $R^8$ are both methyl.

13. A compound according to claim 10, wherein $R^7$ and $R^8$, together with the nitrogen atom to which they are attached, form a pyrrolidine ring.

14. A compound according to claim 1, wherein $R^2$ is a group of Formula V.

15. A compound according to claim 14, wherein $R^5$ and $R^6$ are both H.

16. A compound according to claim 1, which is selected from the group consisting of:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole;
3-(N-Methylpyrrolidin-3-yl)-5-vinyl-1H-indole;
5-Ethynyl-3-(2-pyrrolidinylethyl)-1H-indole;
3-(2-N,N-Dimethylaminoethyl)-5-[2-(thien-2-yl)ethynyl]-1H-indole;
5-{2-[4-(isothiocyanato)phenyl]ethynyl}-3-(2-pyrrolidinylethyl)-1H-indole;
3-(2-Pyrrolidinylethyl)-5-{2-[4-(pyrrol-1-yl)phenyl]ethynyl}-1H-indole;
5-[2-(4-Methylphenyl)ethynyl]-3-(2-pyrrolidinylethyl)-1H-indole;
5-{2-[4-(Isopropylsulfonyl)-2-(methylcarboxylate)-thien-3-yl]ethynyl}-3-(2-pyrrolidinylethyl)-1H-indole;
5-{2-[1-(2-(Ethylsulfonyl)ethyl)-2-methyl-4-nitroimidazol-5-yl]ethynyl}-3-(2-pyrrolidinylethyl)-1H-indole;
5-{2-[2-(Methylthio)phenyl]ethynyl}-3-(2-pyrrolidinylethyl)-1H-indole;
5-[2-(Acetophenon-4-yl)ethynyl]-3-(2-pyrrolidinylethyl)-1H-indole;
3-(2-Pyrrolidinylethyl)-5-[2-(thien-2-yl)ethynyl]-1H-indole; and
5-[2-(5-Chloro-2-methoxyphenyl)ethynyl]-3-(2-pyrrolidinylethyl)-1H-indole.

17. A compound according to claim 16, which is selected from the group consisting of:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole;
3-(N-Methylpyrrolidin-3-yl) -5-vinyl-1H-indole;
5-Ethynyl-3-(2-pyrrolidinylethyl)-1H-indole;
5-{2-[4-(isothiocyanato)phenyl]ethynyl}-3-(2-pyrrolidinylethyl)-1H-indole;
3-(2-Pyrrolidinylethyl)-5-{2-[4-(pyrrol-1-yl)phenyl]ethynyl}-1H-indole;
5-{2-[1-(2-(Ethylsulfonyl)ethyl)-2-methyl-4-nitroimidazol-5-yl]ethynyl}-3-(2-pyrrolidinylethyl)-1H-indole; and
5-[2-(5-Chloro-2-methoxyphenyl)ethynyl]-3-(2-pyrrolidinylethyl)-1H-indole.

18. A compound according to claim 17, which is selected from the group consisting of:
3-[2-(N,N-Dimethylamino)ethyl]-5-vinyl-1H-indole;
3-[2-(N-Pyrrolidinyl)ethyl]-5-vinyl-1H-indole;
(R)-3-[(N-Methylpyrrolidin-2-yl)methyl]-5-vinyl-1H-indole; and
5-Ethynyl-3-(2-pyrrolidinylethyl)-1H-indole.

19. A compound according to claim 18, which is (R)-3-[(N-methylpyrrolidin-2-yl)methyl]-5-vinyl-1H-indole.

20. A pharmaceutical composition, comprising a pharmaceutically acceptable carrier and, in an amount effective to stimulate a 5-$HT_{1D}$-like receptor, a compound as defined in claim 1.

21. A pharmaceutical composition according to claim 20, wherein said compound is one in which $R^1$ is selected from the group consisting of H, thienyl, 4-(isothiocyanato)phenyl, 4-(pyrrol-1-yl)phenyl, 4-methylphenyl, 4-(isopropylsulfonyl)-2-(methylcarboxylate)-thienyl, 1-[2-(ethylsulfonyl)ethyl]-2-methyl-4-nitroimidazol-5-yl, 2-(methylthio)phenyl, acetophenonyl and 5-chloro-2-methoxyphenyl.

22. A pharmaceutical composition according to claim 21, wherein said compound is one in which $R^1$ is H.

23. A pharmaceutical composition according to claim 22, wherein said compound is one in which A is vinyl.

24. A pharmaceutical composition according to claim 20, wherein said compound is one in which $R^2$ is a group of Formula III and $R^4$ is methyl.

25. A pharmaceutical composition according to claim 20, wherein said compound is one in which $R^2$ is selected from the group consisting of Formula IV and Formula V.

26. A pharmaceutical composition according to claim 25, wherein said compound is one in which $R^5$ and $R^6$ are both H.

27. A pharmaceutical composition according to claim 26, wherein said compound is one in which $R^7$ and $R^8$ are both methyl.

28. A pharmaceutical composition according to claim 26, wherein said compound is one in which $R^7$ and $R^8$, together with the nitrogen atom to which they are attached, form a pyrrolidine ring.

29. A method for treating a patient having a medical condition for which a 5-$HT_{1D}$-like receptor agonist is indicated, comprising the step of administering to the patient a pharmaceutical composition as defined in claim 20.

30. A method for treating a patient according to claim 29, wherein the medical condition is migraine.

* * * * *

UNITED STATES PATENT AND TRADEMARK OFFICE
CERTIFICATE OF CORRECTION

PATENT NO. : 5,856,510

DATED : January 5, 1999

INVENTOR(S) : Meng et al.

It is certified that error appears in the above-identified patent and that said Letters Patent is hereby corrected as shown below:

```
On the title page:
     Item [75], line 1, delete "Oingchang" insert therefor -- Qingchang --
```

Signed and Sealed this

Twentieth Day of April, 1999

Attest:

Q. TODD DICKINSON

*Attesting Officer*     *Acting Commissioner of Patents and Trademarks*